US009677065B2

(12) United States Patent
Jaroch et al.

(10) Patent No.: US 9,677,065 B2
(45) Date of Patent: Jun. 13, 2017

(54) CELL-MEDIATED SILICA SOL-GEL ENCAPSULATION OF LIVING CELLS AND TISSUES

(75) Inventors: David Benjamin Jaroch, Lafayette, IN (US); Jenna Leigh Rickus, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 13/386,356

(22) PCT Filed: Jul. 21, 2010

(86) PCT No.: PCT/US2010/042672
§ 371 (c)(1),
(2), (4) Date: Apr. 2, 2012

(87) PCT Pub. No.: WO2011/011468
PCT Pub. Date: Jan. 27, 2011

(65) Prior Publication Data
US 2012/0178137 A1 Jul. 12, 2012

Related U.S. Application Data

(60) Provisional application No. 61/227,230, filed on Jul. 21, 2009.

(51) Int. Cl.
*C12N 11/14* (2006.01)
*C04B 38/06* (2006.01)
*C12M 1/12* (2006.01)

(52) U.S. Cl.
CPC .......... *C12N 11/14* (2013.01); *C04B 38/065* (2013.01); *C04B 38/0695* (2013.01); *C04B 2235/3418* (2013.01); *C12M 25/14* (2013.01)

(58) Field of Classification Search
USPC ...................................................... 435/174
See application file for complete search history.

(56) References Cited

U.S. PATENT DOCUMENTS

| 4,797,358 | A | 1/1989 | Motai et al. ................. 435/176 |
| 5,286,495 | A | 2/1994 | Batich et al. ................. 424/490 |
| 5,998,162 | A | 12/1999 | Cappelletti et al. ........... 435/41 |
| 6,214,593 | B1 | 4/2001 | Carturan et al. .............. 435/176 |
| 6,303,290 | B1 * | 10/2001 | Liu et al. ......................... 435/4 |
| 6,387,453 | B1 | 5/2002 | Brinker ......................... 427/387 |
| 6,495,352 | B1 | 12/2002 | Brinker et al. |

FOREIGN PATENT DOCUMENTS

| JP | 2003-088747 | 3/2003 |
| JP | 2003-325638 | 11/2003 |
| WO | WO 2008-045145 A2 | 4/2008 |
| WO | WO 2008/057709 | 5/2008 |
| WO | 2011088155 A2 | 7/2011 |

OTHER PUBLICATIONS

Ferrand et al. Water diffusion in the simulated French nuclear waste glass SON 68 contacting silica rich solutions: experimental and modeling. Journal of Nuclear Materials. 2006;355:54-67.*
Branyik et al. Encapsulation of microbial cells into silica gel. Journal of Sol-Gel Science and Technology. 1998;13:283-287.*
Peterson et al. Silica sol-gel encapsulation of pancreatic islets. P.S.E.B.M. 1998;218:365-369.*
Pope et al. Bioartificial organs I: silica gel encapsulated pancreatic islets for the treatment of diabetes mellitus. Journal of Sol-GEI Science and Technology. 1997;8:635-639.*
Kuncova et al. Monitoring of the viability of cells immobilized by sol-gel process. Journal of Sol-Gel Science and Technology. 2004;31:335-342.*
Premkumar et al. Encapsulation of luminous recombinant *E. coli* in sol-gel silicate films. Adv. Mater. 2001;13(23):1773-1775.*
Avnir et al. Recent bio-applications of sol-gel materials. J. Mater. Chem. 2006;16:1013-1030.*
Jovica D. Badjic and Nenad M. Kostic, "Effects of Encapsulation in Sol-Gel Silica Glass on Esterase Activity, Conformational Stability, and Unfolding of Bovine Carbonic Anhydrase II," Chem. Mater., vol. 11 (12), pp. 3671-3679, Nov. 24, 1999.
Laurie Bergogne et al., "Bio-Encapsulation within Sol-Gel Glasses," Molecular Crystals and Liquid Crystals, vol. 354, pp. 79-89, Dec. 1, 2000.
Christophe F. Meunier et al., "Encapsulation of cells within silica matrixes: Towards a new advance in the conception of living hybrid materials," Journal of Colloid and Interface Science vol. 342, pp. 211-224, Oct. 25, 2009.
International Searching Authority, International Search Report for PCT/US2010/042672, Mar. 30, 2011.
International Searching Authority, Written Opinion for PCT/US2010/042672, Mar. 30, 2011.
International Searching Authority, International Preliminary Report on Patentability for PCT/US2010/042672, Jan. 24, 2012.
Kuncova, G., et al; "Monitoring of the Viability of Cells Immobilized by Sol-Gel Process"; Journal of Sol-Gel Science and Technology, Aug. 1, 2004, vol. 31, No. 1-3, pp. 335-342.
Brinker, C. Jeffrey,et al.; "The Physics and Chemistry of Sol-Gel Processing"; Academic Press, Inc.; Chapter 5, pp. 303-304; Publishers, Harcourt Brace Jovanovich.
Brinker, C. Jeffrey,et al.; "The Physics and Chemistry of Sol-Gel Processing"; Academic Press, Inc.; Chapter 13, pp. 796-797; 834-841; Publishers, Harcourt Brace Jovanovich.
Avnir et al., "Recent Bio-Applications of Sol-Gel Materials", *J. Mater. Chem.*, 16:1013-1030, 2006.
Boninsegna et al., "Encapsulation of Individual Pancreatic Islets by Sol-Gel SiO2: A novel procedure for perspective cellular grafts", *Journal of Biotechnolgoy*, 100:277-286, 2003.

(Continued)

*Primary Examiner* — Lynn Y Fan
(74) *Attorney, Agent, or Firm* — Purdue Research Foundation; Yonghao Hou

(57) ABSTRACT

Methods are provided for the encapsulation of living cells with a silica glass layer. The methods comprise adding a sol solution to cells in buffered media, forming a sol-gel layer on the cells and then diluting the media or removing the cells from the media.

13 Claims, 7 Drawing Sheets

(56) References Cited

OTHER PUBLICATIONS

Figure 1:
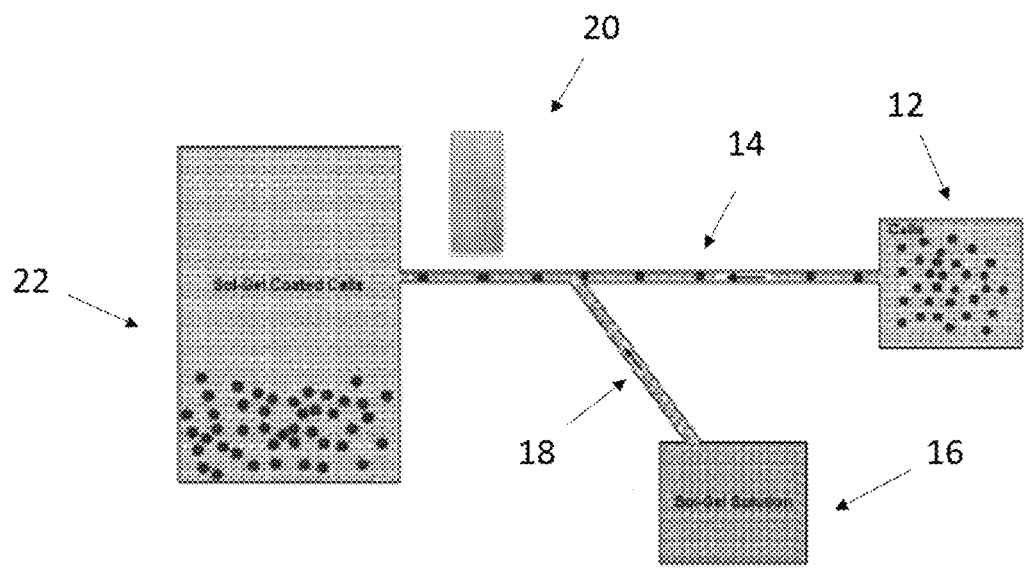

Carturan et al., "Encapsulation of Functional Cells by Sol-Gel Silica: Actual Progress and Perspectives for Cell Therapy", *J. Mater. Chem.*, 14:2087-2098, 2004.

Carturan et al., "Encapuslation of viable animal cells for hybrid bioartificial organs by the Biosil method", *Optical Science Engineering and Instrumentation*, p. 366-373, 1997.

Coradin et al., "Silica-Alginate Composites for Microencapsulation", *Applied Microbiology and Biotechnology*, 61:429-434, 2003.

Groger et al., "Biomolecular self-assembly and its relevance in silica biomineralization", *Cell Biochemistry and Biophysics*, 50:23-39, 2008.

International Preliminary Report on Patentability issued in PCT Application No. PCT/US2011/021032, mailed Jul. 17, 2012.

International Search Report and Written Opinion issued in PCT Appl. No. PCT/US2009/048665, completed Aug. 4, 2009.

International Search Report and Written Opinion issued in PCT Application No. PCT/US2011/021032, mailed Oct. 25, 2011.

Jaroch et al., "Cell-mediated deposition of porous silica on bacterial biofilms", *Biotechnology and Bioengineering*, 108:10:2249-2259, 2011.

Kroger et al., "Polycationic peptides from diatom biosilica that direct silica nanosphere formation", *Science*, 286:1129-1132, 1999.

Slowing et al., "Mesoporous Silica nanoparticles for Drug Delivery and Biosensing Applications", *Advanced Functional Materials*, 17:1225-1236, 2007.

Wei et al., "Encapsulation of enzymes in mesoporous host materials via the nonsurfactant-templated sol-gel process", *Materials Letters*, 44:6-11, 2000.

Xomeritakis et al., "Aerosol-Assisted Deposition of Surfactant-Templated Mesoporous Silica Membranes on Porous Ceramic Supporters", *Microporous and Mesoporous Materials*, 66:91-101, 2003.

Brinker, Sol-Gel Science, The Physics and Chemistry of Sol-Gel Processing; Academic Press, Inc.; pp. 3-5; 99.

Jarrold, "Peptides and proteins in the vapor phase", *Annual Review of Physical Chemistry*; 51(1):179-207, 2000.

Nash et al., "Human embryonic stem cell model of ethanol-mediated early developmental toxicity", *Experimental Neurology*, 234(1):127-135, 2012.

Rickus et al., "Photochemical Coenzyme Regeneration in an Enzymatically Active Optical Material", *The Journal of Physical Cheminstry B*; 108(26):9325-9332, 2004.

Rickus et al., "Enzyme-Doped Thin Films and Optical fiber Sensors for Glutamate", *Proceedings in SPIE*, 2002.

Rickus et al., "Photochemical enzyme co-factor regeneration: Towards continuous glutamate monitoring with a Sol-Gel Optical Biosnsor ", *Materials Research Society Symposium Proceedings*, 723:155-160, 2002.

Lisa M. Ellerby, et al.; "Encapsulation of Proteins in Transparent Porous Silicate Glasses Prepared by the Sol-Gel Method"; American Association for the Advancement of Science; Science, New Series, vol. 255, No. 5048 (Feb. 29, 1992) pp. 1113-1115.

Rakesh K. Jain, et al,; "Engineering Vascularized Tissue"; Nature Biotechnology, vol. 23, No. 7; Jul. 2005.

Kahn et al. "Collagen-fibril matrix properties modulate the kinetics of silica polycondensation to template and direct biomineralization," Biomineralization and Biomimetics Articles, J. Mater. Res., Feb. 15, 2016, vol. 31, No. 3, pp. 311-320.

Premkumar et al., Antibody-based immobilization of bioluminescent bacterial sensor cells, Talanta, Aug. 20, 2001, No. 55, pp. 1029-1038.

\* cited by examiner

123456789012345678901234567890123456789012345678901234567890
CELL-MEDIATED SILICA SOL-GEL ENCAPSULATION OF LIVING CELLS AND TISSUES

CROSS-REFERENCE TO RELATED APPLICATIONS

This application is a 371 nationalization of PCT Application No. PCT/US2010/042,672, filed Jul. 21, 2010, and claims the benefit of U.S. provisional Application No. 61/227,230, filed Jul. 21, 2009, the entire disclosures of which are expressly incorporated herein by reference.

BACKGROUND OF THE INVENTION

The present invention relates generally to sol-gel processes and more particularly to encapsulation of living cells using sol-gel processes.

Recent advances in technology have allowed for the integration of man-made substances with cellular materials to create a new class of living composite devices. Such devices have the ability to respond dynamically with biological functionality to their local environment.

One potential class of synthetic material for hybrid cellular applications is sol-gel derived silica glasses. Such materials are biocompatible in soft and hard tissue applications. Silica based sol-gels also possess a mesoporous architecture, allowing free diffusion of small molecules while preventing penetration of larger structures such as cells. Sol-gels can be synthesized at room temperature in aqueous environments with specialized formulations capable of generating non-cytotoxic liquid intermediate sols.

Traditionally cell immobilization using sol-gel methods results in cell entrapment within bulk materials creating significant diffusion barriers. Current technology to create thin coatings around cells required aerosolizing processes to apply silica based sol-gels to biological materials. The aerosolizing processes require vaporizing the sol-gel precursors and then contacting the vapor to the cell surface. These processes are inefficient, expensive, and are limited in the types of silica precursors and co-dopants that can be used. In addition only a 2D planar entrapment layer is formed.

Therefore it would be desirable to have a method for forming thin sol-gel layers on biological materials and cells that is efficient, cost effective, simple, able to create 3D thin layers, and flexible for entrapment of a range of materials from single cells to tissues.

SUMMARY OF THE INVENTION

In one aspect of the present invention there is provided a method for encapsulating cells comprising the steps of adding silica rich sol solution to cells in a buffered media, monitoring cells for the formation of a silica layer on the cells and isolating the cells from the silica solution after the silica layer is observed.

In another aspect of the present invention there is provided a method for encapsulating cells comprising the steps of flowing buffered media and cells from a first reservoir to a second reservoir through a channel, wherein the channel has a diameter about the same as that of an individual cell and wherein the second reservoir comprises buffered media, introducing a silica rich sol solution into the channel with the cells, allowing a sol-gel layer to form on the cells after the introduction of the sol solution and diluting the cells in the buffered media of the second reservoir.

These and other features, aspects and advantages of the present invention will become better understood with reference to the following drawings, description and claims.

BRIEF DESCRIPTION OF THE DRAWINGS

FIG. 1 is a schematic illustrating a method for encapsulating cells with a sol-gel layer, according to one embodiment of present invention;

FIG. 2A is a scanning electron micrograph of undifferentiated mouse P19 cells;

FIG. 2B is a scanning electron micrograph of undifferentiated mouse P19 cells exposed to a saturated silica environment;

FIG. 3 is graph showing proton flux measurements of undifferentiated mouse P19 cells exposed to a saturated silica environment;

FIG. 4 is a scan showing cyclic glucose influx patterns into silica-entrapped and non-silicated INS1 cells compared to HITβ cells;

FIG. 5A is a schematic showing an example of a silica-encapsulated biofilm of a hollow fiber membrane bioreactor;

FIG. 5B is a cross-section of the silica-encapsulated biofilm of a hollow fiber membrane bioreactor of FIG. 5A;

FIG. 6A is a bar graph showing the stress response before and five hours after cell-mediated encapsulation using trifluoroacetic acid;

FIG. 6B is a bar graph showing the stress response before and five hours after cell-mediated encapsulation using hydrochloric acid;

FIG. 6C is a bar graph showing the stress response before and five hours after cell-mediated encapsulation using nitric acid;

FIG. 7A is a scanning electron micrograph of a *N. europaea* biofilm surface without silica deposition;

FIG. 7B is a scanning electron micrograph of a *N. europaea* biofilm surface 30 minutes after silica encapsulation;

FIG. 7C is a scanning electron micrograph of a *P. aeruginosa* biofilm surface without silica deposition;

FIG. 7D is a scanning electron micrograph of a *P. aeruginosa* biofilm surface 30 minutes after silica encapsulation;

FIG. 8A is an EDX spectra of a *N. europaea* biofilm surface without silica deposition;

FIG. 8B is an EDX spectra of a *N. europaea* biofilm surface 30 minutes after silica encapsulation;

FIG. 8C is an EDX spectra of a *P. aeruginosa* biofilm surface without silica deposition;

FIG. 8D is an EDX spectra of a *P. aeruginosa* biofilm surface 30 minutes after silica encapsulation;

FIG. 9A is a bar graph showing the oxygen and substrate influx for *N. europaea* before and after silica encapsulation; and FIG. 9B is a bar graph showing the oxygen and substrate influx for *P. aeruginosa* before and after silica encapsulation.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention provides methods for encapsulating cells in silica glass by adding a saturated silica solution (the sol solution) directly to a buffered media comprising the cells. After the addition of the sol solution, the cells are monitored for formation of a sol-gel layer. Once the sol-gel layer is observed, the cells are then isolated from the silica-containing buffered media. The sol-gel layer may complete gelation (polycondensation) after the isolation of the cells. This method allows for the encapsulation of living cells, both prokaryotic and eukaryotic, for use in sensors or as adaptive drug delivery devices. The current system allows for the implantation of foreign cellular material into a host without the need for global suppression of the immune system of the host.

Porous silica encapsulation of cells may result in material properties with specific advantages for the application to cellular transplant therapies. First, Silica sol-gels are bioactive materials that integrate with the surrounding tissue forming a biocompatible interface. This interaction with native tissues prevents the formation of a thick capsule that can limit diffusion reduce the efficacy of transplanted tissue, Second, the resulting materials may possess high pore volumes but with mesoscale pore sizes (2-50 nm) similar to those produced by solution sol-gel methods thus enabling good transport of small molecules through the materials while securely encasing cells. Third, swelling of a cell immobilization matrix can result in cell loss. Unlike immobilization using soft materials, such as hydrogels, the porous silica layers will not swell; therefore cell entrapment is maintained over time. Fourth, because the sol-gel synthesis results in the formation of a solid matrix from liquid precursors, the solid can be formed on complex geometries. This feature will be extremely useful for coating suspended cells or cells cultured on 3D scaffolds. Fifth, the thickness of the biomineral layer can be controlled by the duration of exposure to the mineralizing environment. Films may range in thickness from 100-200 nm to several microns. Compared to bulk materials, thin (nano) and thick (micro) films have the advantage of not creating additional diffusion barriers that could limit transport. Sixth, the breakdown product of silica-based biominerals is primarily silicic acids. These small molecules are naturally occurring in many organs (including bone, kidneys, liver) and are well tolerated by living organisms including humans. Finally, silica biomaterials have good optical properties in the UV and visible spectra allowing for characterization and monitoring of the underlying cells and substrates.

It has been found that the proteins and carbohydrates on the cell surface serve as nucleation points for the deposition of silica, causing the formation of a mesoporous amorphous silica glass around the cells. In silica-containing buffered media, silica is attracted to the cell membrane, forming a sol-gel layer. The sol-gel layer continues the polycondensation of the silica particles in the sol-gel to form the silica glass layer around the cells. The natural concentration of the silica sol-gel on the cell membrane allows for the polycondensation of the silica particles in the sol-gel to form the silica glass layer around the cells without having to remove the solvent. In contrast, the methods of the prior art require converting the silica sol to an aerosol that is applied across the surface of the cells, forming a sol-gel layer. The solvent is then removed, allowing for the polycondensation of silica particles to form the silica glass layer.

In one embodiment, the present invention provides a method for encapsulating cells in a silica glass layer comprising the steps of adding a silica rich sol solution to cells in a buffered media, monitoring cells for the formation of a silica layer on the cells and isolating the cells from the silica-containing media after the sol-gel layer is observed. The method of the present invention is applicable to individual (dissociated) cells, cellular clusters or tissue. When referring to "cells" herein, all types of cells, cellular cluster and/or tissue samples are contemplated. The cells may be prokaryotic or eukaryotic. The cells may be, for example, bacterial, fungal, yeast, mammalian, plant or animal cells. Moreover the cells may be naturally occurring or they may be cloned or recombinant cells.

Sol solutions for the sol-gel process are well known in the art. The silica rich sol solution may be prepared by any of a number of routes. These include but are not limited to the acid or base catalyzed hydrolysis of organo-silicon compounds such as tetramethyl orthosilicate (TMOS). tetraethyl orthosilicate (TEOS), tetrabutyl orthosilicate, tetrapropyl orthosilicate, tetraallyl orthosilicate, tetrakis(dimethylsilyl) orthosilicate, tetraamyl orthosilicate, tetrahexyl orthosilicate, tetraisopropyl orthosilicate, tetraoctyl orthosilicate, and tetraphenyl orthosilicate. Alternatively, the sol solution may be prepared by direct preparation from readily soluble silica salts such as sodium silicate. In an exemplary embodiment the sol solution has a silica concentrations of from about 100 ppm (the solution saturation point) to about 1000 ppm, from about 80 ppm to about 10,000 ppm or from about 100 ppm to about 100,000 ppm. The working time of the sol solution should be considered in preparing the sol solution. Polycondensation of the silica monomers to small particles and subsequently to more extensive gel networks begins in the sol solution. The more highly saturated the solution, the more unstable it will be and will rapidly condense. The amount of solution added to the buffered media required to induce cell-mediated silication should also be considered. The final silica concentration in the cell-containing buffered media must near or above saturation levels.

The following is a non-limiting example of the preparation of a representative silica rich sol solution. A silica sol mixture with an excess of $H_2O$ (i.e. 1 to 12 mol ratio of tetramethyl orthosilicate (TMOS) to $H_2O$) is first catalyzed under agitation in a sonicator at room temperature using a very low concentration of acid so as to minimize shift in cellular pH when the sol solution is added to the cell-containing buffered media. The resultant sol contains a weakly acidic mixture of methanol, $H_2O$, and Si—O groups. Water in excess of that needed to completely hydrolyze the organo-silicon compound is used to slow the polycondenstation of silica into a solid mass. Typical concentrations range from a 4:1 $H_2O$:TMOS mol ratio to a 40:1 mol ratio. Higher concentrations of water will slow polycondenstation but will require larger volumes in order to saturate cell culture solutions.

The hydrolysis of the organo-silicon compound may be acid or base catalyzed. In this example, the compound is acid catalyzed. Very small quantities of an acid initiator are utilized in order to minimize the pH disturbance to buffered cell media upon addition. The acid may be, but not limited to trifluoroacetic acid, hydrochloric acid or nitric acid. An example quantity of HCl would be the addition of 50 µl of 0.04 M HCl solution to 50 ml of TMOS/$H_2O$ mixture. This quantity may be adjusted to speed hydrolysis by adding greater quantities of acid. Care must be taken to prevent stress on cells due to an acidic environment. For example, a typical mammalian cell line must be maintained within a pH range of 7-7.8. Bacterial, yeast, and plant cells will have different ranges of tolerance to acidic conditions. The amount of acid used to catalyze the hydrolysis reaction must not acidify the buffered culture media to the point of killing cells during silification. The skilled artisan without undue experimentation can determine the amount of acid required.

Before the addition of the sol solution to the cells, the methanol is removed by rotary evaporation, generating a supersaturated, slightly acidic, silica solution. The hydrolysis reaction products, often alcohols, are typically toxic and must be removed prior to introduction in cell culture media. Different organo-silicon compounds will have reaction products with different levels of toxicity. TMOS was chosen for the current example because the methanol can be easily removed from aqueous solution by means of rotary evaporation. Different precursors can be used to minimize cell stress due to residual reaction products.

In another embodiment of the present invention cells are present in a buffered media, the media selected for optimal growth and/or maintenance of the cells. The sol solution is added to the buffered media, creating a supersaturated cell and media composition with the silica. The number of cells is not critical and may vary from a single cell to large clusters of cells or even tissue. In one exemplary embodiment, the amount of silica in the buffered media may be from about 50 ppm to about 50,000 ppm, 80 ppm to about 10,000 ppm or from about 100 ppm to about 1000 ppm. It will be appreciated that the concentration is directly related to the sol-gel layer formation. Cell mediated silica layer formation is slower at lower silicon concentrations. Higher concentrations induce rapid layer formation, but can prove toxic to cells and may induce the bulk gelation of the culture media. The desired concentration of silica may be determined without undue experimentation.

In another embodiment, the cells are monitored for the formation of sol-gel layer after addition of the sol solution. Cell-mediated sol-gel layer formation may occur from about 1 minute to about 1 hour after sol addition, depending on initial silica concentration. In an exemplary embodiment, the sol-gel layer formation occurs within 15 minutes. A number of additives, such as phosphate ions and serum proteins, may be incorporated into the media in order to speed the sol-gel polycondensation reaction. Layer formation may be monitored by light microscopy. Other non-limiting methods for confirming layer formation include Raman microscopy, Fourier transform infrared microscopy (FTIR), fluorescence microscopy, scanning electron microscopy, and energy dispersive X-ray spectroscopy.

In yet another embodiment, the cells must be removed, or alternatively, the media must be diluted below the silica saturation point, immediately after silica layer formation is confirmed. Over time the silica will continue to polycondense and a bulk gel will form throughout the media if it is not diluted.

Figure 2A:
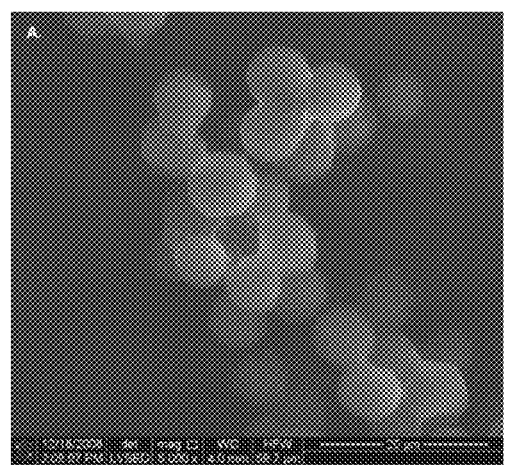
Figure 2B:
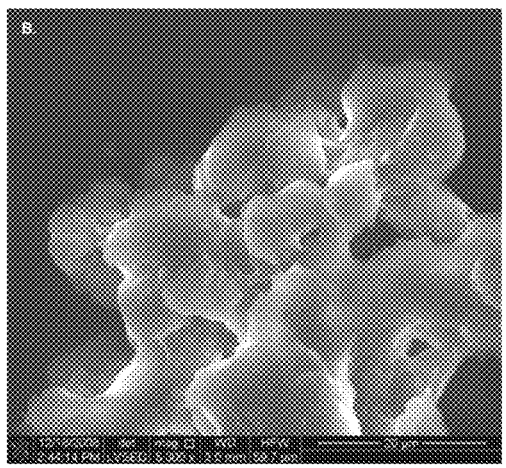
Figure 3:
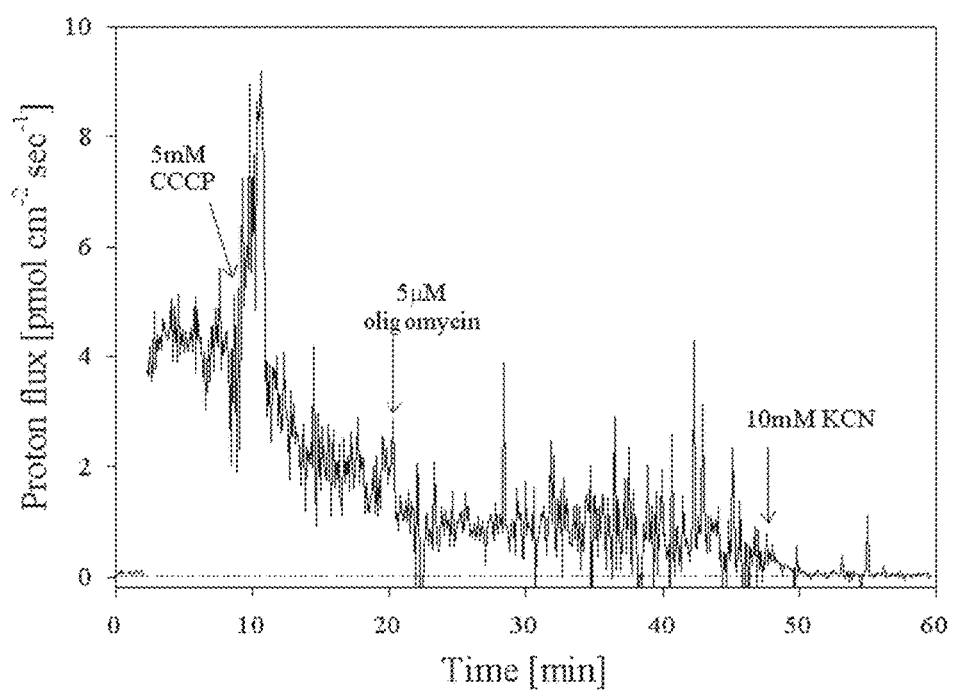

Experiments conducted on suspended mouse (P19) cells demonstrated that the endogenous proteins and polysaccharides of mammalian cells can serve as a preferential site for silica polycondensation, mediating the formation of a silica layer (FIGS. 2A and 2B). Live cell staining of these clusters demonstrated that the cells survive immersion in mineralizing environments and retain intercellular esterase activity as evidence by green fluorescence in live cell stains. Cellular activity was also confirmed by proton flux measurements taken at the silica membrane surface (FIG. 3). Proton flux increased following addition of 5 µM-CCCP (a proton ionosphere), as the proton gradient established by the active cells was disrupted by the uncoupler. Subsequent addition of oligomycin inhibited ATP syntase (reducing proton flux), and addition of 10 mM KCN abolished proton motive force and aerobic respiration. These results indicate that physiology and stress response mechanisms are similar to non-encapsulated cells. The silica is deposited on the external membrane of the cell. During this process cells are expected to experience some level of stress. A membrane integrity assay was conducted using propidium iodide stain. The results of this assay indicate that the encapsulation process does induce membrane permeability shortly after biomineralization. After incubation, cells are able to repair disruptions to the membrane and return to normal integrity.

The silica was deposited on the external membrane of the cell. During this process cells are expected to experience some level of stress. A membrane integrity assay was conducted using propidium iodide stain. The results of this assay indicate that the encapsulation process does induce membrane permeability shortly after biomineralization. After incubation, cells are able to repair disruptions to the membrane and return to normal integrity.

Figure 4:
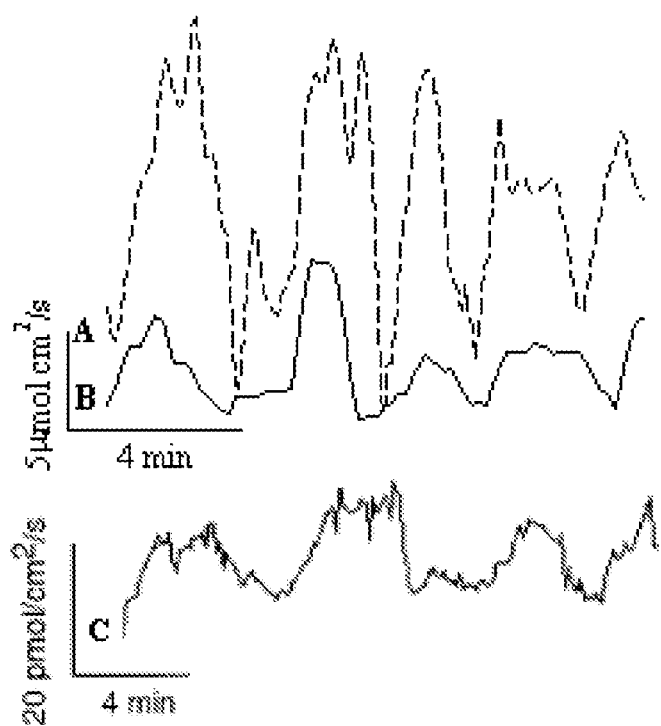

A number of refinements may be made to the mineralizing solution in order to improve cellular response. Silica concentration, deposition rate and mineral layer thickness are expected to strongly influence both the initial cellular stress response and long term viability. The nanostructure of solution-based silica deposits, which governs the diffusion characteristics of the encapsulant, can be influenced by several factors including silica concentration, and acid initiator species (Brinker, C. J. et al., (1990) Sol-gel Science). Through an iterative process of parameter adjustment and cell viability screening, encapsulated cell performance will be maximized. We will also explore the use of additive such as polyethylene glycol, which has been shown to accelerate and enhance the membrane resealing process in neuronal membranes after mechanical damage In a preliminary study, adherent rat pancreatic β (INS-1) cells were subjected to a biomineralizing solution. Glucose responsiveness was then assessed using a self-referencing glucose sensor according to Shi et al. and Porterfield (Shi, J. et al., (2008) Proceedings of the Institute of Biological Engineers Annual Conference, Chapel Hill, N.C.; Porterfield, D. M. (2007) Biosensors and Bioelectronics 22 (7), 1186-1196) (FIG. 4). INS-1 cells demonstrate cyclic glucose intake prior to and after biomineralization which is similar to cyclic oxygen patterns in HIT β cells (Porterfield, D. M. et al. (2000) Diabetes 49 (9), 1511-1516. The cells were responsive to glucose stimulation, displaying regular influx patterns after bolus introduction of additional glucose and eventually stabilizing in a cyclic pattern with an average oscillation period (3.48±0.28 minutes) similar to that reported for HIT β cells (3.2 minutes).

In an alternate embodiment, the present invention provides a method for encapsulating living cells in a silica glass layer using microfluidic devices. The cells have a tendency to clump during the early stages of sol-gel layer formation and the use of microfluidic devices may eliminate this. As illustrated in FIG. 1, the method comprises the steps of flowing buffered media and cells from a first reservoir 12 to a second reservoir 22 through a first channel 14, wherein the first channel 14 has a diameter about the same as that of an individual cell and wherein the second reservoir 22 comprises buffered media. The sol solution is introduced into the first channel 14 from a third reservoir 16 through a second channel 18. The concentration of the sol solution is similar to that described above. As the cells move through the first channel 14, a sol-gel layer forms on the cells after the introduction of the silica solution. Finally, the cells are deposited in the second reservoir 22 where the cells are diluted in the buffered media of the second reservoir 22. It may be desirable to have a monitor 20 situated downstream from the second channel 18 to monitor sol-gel layer formation on the cells. The flow rate may be adjusted to allow sufficient time for layer formation prior to dilution of the cells in the second reservoir 22. The formation and the properties of the sol-gel layer are governed by flow rate, sol concentration, and the duration of the reaction with the sol mixture.

In a further embodiment, the surface of the sol gel layer can be modified using the peptide ormosils, as described in PCT patent application serial number PCT/US2007/081122, incorporated herein in its entirety. These agents can be used to prevent apoptosis of the encapsulated cells, locally suppress the immune system, and support tissue integration at the sol-gel interface.

It should be appreciated that the encapsulated cells are able to survive and maintain functionality under the silica glass layer described herein. The mesoporous architecture of the sol allows transport of nutrients into the cells. Useful cellular products, such as hormones, neurotransmitters, or other signaling molecules, can also diffuse from the cells into surrounding tissue or material environment. The silica glass layer serves as a physical barrier to the immune system when implanted, limiting cell rejection.

EXAMPLES

Example 1

Embryonic carcinoma derived stem cells (the P19 cell line) were induced to differentiate. Four plates of differentiated P19 cells were started and the free-floating multicell bodies were collected from the media of all four plates. The cells were centrifuged and the cells from all four plates were pooled into a single 10 ml volume. Care was taken to prevent dissociation of the cell clusters. Retention of the clusters was confirmed visually by microscope.

A sol-gel was prepared by catalyzing the hydrolysis of 14.2 g of TMOS in 21.6 g of deionized water using 100 µl of 0.04M HCl with sonication for 15 minutes. The methanol by-product of the hydrolysis reaction was removed by rotary evaporation at 35° C. for about 5-6 minutes. Finally, the solution was filtered through a 0.2 µm syringe filter prior to use.

1 ml of concentrated P19 (embryonic carcinoma) cell clusters were pipetted into a multiwell plate and a 100 µl of the sol solution was added. The cell clusters and sol solution were mixed by rocking the plate.

The sol dropped to the bottom of the well and solidified. It is believed that agitation did not occur early enough to disperse the sol. Cells were imbedded in the sol layer on the bottom of the well, but the sol-gel layer that formed was not specific to the cells.

Example 2

The cells and sol solution were prepared as described in Example 1. 1 ml of concentrated P19 cell clusters were pipetted into a multiwell plate and a 50 µl of the sol solution was added dropwise while the media was agitated with the addition of the sol. After 10 minutes the cell clusters appeared to round over and develop a very thing layer of sol around the cells. The layer was difficult to see. After about 15-20 minutes the clusters began to clump together and move in a collective manner when the solution was agitated. This is indicative of a sol-gel layer on the cell clusters. After and addition 45-60 minutes, the entire cell solution began to gel.

Example 3

The cells and sol solution were prepared as described in Example 1. 1 ml of concentrated P19 cell clusters were incubated with 50 µl of phosphate buffered saline (PBS) for 15 minutes before the addition of the sol solution. 50 µl of the sol solution was then added as described in Example 2.

A more rapid formation of the sol-gel layer was observed and very tight cell clusters were formed. There was a dark corona layer around the clusters. The cells began to clump after 15-20 minutes and eventually only clumps of cell clusters were present, composed of 4-6 distinct clusters of cells. The phosphate appeared to encourage sol-gel formation around the clusters specifically and layer formation was more rapid than in the absence of the PBS. The addition of PBS also appeared to inhibit bulk gelation and the media remained fluid for over an hour.

Example 4

The cells and sol solution were prepared as described in Example 1. 1 ml of concentrated P19 cell clusters were incubated with 100 µl of phosphate buffered saline (PBS) for 15 minutes before the addition of the sol solution. 50 µl of the sol solution was then added as described in Example 2.

The results were similar to those of Example 3, although the sol-gel layer on the cell clusters appeared less defined and the cells did not clump as well. The sol-gel may have catalyzed too rapidly in the presence of the increased phosphate ion concentration, leading to the non-visible formation of sol-gel grains as opposed to the desired bulk gelation.

Example 5

Undifferentiated P19 cells from an 80% confluent plate were trypsinized and centrifuged. 2 ml of media was added the pelleted cells were resuspended. 1 ml of the cells were added to a multi-well plate. The cells were observed to be present in very high concentration, typically singularly or in clusters of 2-3 cells. 50 µl of the sol solution was then added as described in Example 2.

The cells initially appeared to be unaffected by the sol solution. An additional 50 µl of the sol solution was added as before. The cells began to clump rapidly. There was obvious functional sol-gel formation as demonstrated by cell clumping and collective movement of the cell clusters.

500 µl of the cell/sol mixture was transferred into another well and 1 ml of fresh media was added to prevent gelation. The cells continued to clump into a couple of massive bodies of cells. The media did not gel after the dilution whereas the undiluted cells and media gelled after 15 minutes.

Example 6

In this example, monoculture *Pseudomonas aeruginosa* and *Nitrosomonas europaea* biofilms (commonly employed in bioreactors for wastewater treatment) are exposed to silica precursors under different acid conditions. SEM imaging and electron dispersive x-ray (EDX) elemental analysis revealed the presence of a thin silica layer covering the biofilm surface. Cell survival was confirmed using confocal imaging (membrane integrity stain) and physiological flux measurements of oxygen, glucose, and $NH_4^+$. No statistical differences in viability, oxygen flux, or substrate flux were observed after encapsulation in silica glass. The results of this study indicate that the thin regular silica membrane permits the diffusion of nutrients and cellular products, supporting continued cellular viability after biomineralization. This technique offers a means of controllably encapsulating biofilms over large surfaces and complex geometries. The generic deposition mechanism employed to form the silica matrix can be translated to a wide range of biological material and represents a platform encapsulation technology.

The cell mediated solution phase encapsulation technique described in this example was developed as a simple scalable means of immobilizing cells within a custom fit film formed at physiological temperatures for a variety of industrial and environmental applications. Biofilms formed by the bacteria *Pseudomonas aeruginosa* and *Nitrosomonas europaea* were selected as a model system for this study due to their widespread distribution in the environment, and use in wastewater treatment/bioremediation. Both organisms are present in soil, sewage, and freshwater systems and are commonly used as model Gram negative bacteria in conventional bioreactors. The two bacteria were grown in monoculture biofilms on hollow fiber membrane aerated bioreactors prior to encapsulation (McLamore, E. et al. (2007) J. Membrane Sci. 289 (1-2), 110-116). Electron microscopy and elemental analysis were used to validate silica layer formation on mature biofilms after exposure to mineralizing solutions. Measurements of substrate (glucose or $NH_4^+$) flux were used to characterize the viability and physiology of the biofilms after silica formation under different synthesis conditions.

Bacterial Cell Culture: *Pseudomonas aeruginosa* is a chemohetertrophic gram negative opportunistic pathogen of animals, plants, and humans, and is used extensively as a model organism in wastewater treatment, bioremediation, and biomedical applications. *P. aeruginosa* (ATCC 97) was obtained from American Type Culture Collection (Manassas, Va.), and biofilms were grown at 37° C. in modified glucose media (10 mM glucose, 50 mM HEPES, 3 mM $NH_4Cl$, 43 mM NaCl, 3.7 mM $KH_2PO_4$, 1mM $MgSO_4$, and 3.5 µM $FeSO_4$).

*Nitrosomonas europaea* is a chemoautotrophic gram negative bacteria that is often the rate limiting step in nitrogen cycling within the environment. *N. europaea* are sensitive to changes in nutrient conditions, light, temperature, and chemical toxins, and thus are widely studied in soil, sewage, and freshwater systems. *N. europaea* (ATCC 19718) was obtained from ATCC, and biofilms were grown in ATCC medium 2265 (25.0 mM-$(NH_4)_2SO_4$, 43.0 mM-$KH_2PO_4$, 1.5 mM-$MgSO_4$, 0.25 mM-$CaCl_2$, 10 µM-$FeSO_4$, 0.83 µM-$CuSO_4$, 3.9 mM-$NaH_2PO_4$, and 3.74 mM-$Na_2CO_3$).

All cells were cultured on semi-permeable silicon membranes in a hollow fiber membrane aerated bioreactor and grown under aerobic conditions according to McLamore et al. (2007). Intact, mature biofilms were extracted from the bioreactors via ¼" ferrules, and transferred to constructed flowcells prior to biosilification according to McLamore et al. 2009 (McLamore, E. et al. (2009) Biotech. Bioeng. 102 (3), 791-799).

Enriched Silica Solution Preparation: Tetramethyl orthosilicate (TMOS, Sigma-Aldrich) was hydrolyzed in a 1:16 mol ratio (TMOS:$H_2O$) deionized water solution using 1 µl of 0.04 molar acid initiator (hydrochloric, nitric, or trifluoroacetic acid) per 1 g of solution. The mixture was stirred vigorously for 10 minutes until clear. The methanol produced by the hydrolysis reaction was removed from the solution by rotary evaporation under vacuum at 45° C. (30% reduction in solution volume). The resulting saturated silica solution was refrigerated prior to use or used immediately.

Physiological Sensing of Oxygen, Glucose and $NH_4^+$: To measure real time flux of metabolic analytes, a sensing technique known as self-referencing (SR) was used (Porterfield, D. M. (2007) Biosensors and Bioelectronics 22 (7), 1186-1196). SR converts concentration sensors into dynamic biophysical flux sensors for quantifying real time transport in the cellular to whole tissue domain, and has been used in many fields, including: agricultural, biomedical, and environmental applications. SR discretely corrects for signals produced by ambient drift and noise by continuously recording differential concentration ($\Delta C$) while oscillating a microsensor between two locations separated by a fixed excursion distance ($\Delta X$), and calculating analyte flux using Fick's first law of diffusion (Kuhtreiber, W. M. et al. (1990) J. Cell Biol. 110 (5), 1565-1573).

SR sensors were used to non-invasively quantify biofilm oxygen and substrate flux using established methods. (McLamore, E. et al. (2009) Biotech. Bioeng. 102 (3), 791-799). Briefly, oxygen flux was measured using a SR optical oxygen sensor, which was constructed by immobilizing an oxygen-quenched fluorescent dye (platinum tetrakis pentafluoropheynl porphyrin) on the tip of a tapered optical fiber. For *P. aeruginosa* biofilms, substrate (glucose) flux was amperometrically measured using a glucose biosensor that was fabricated by entrapping glucose oxidase within a Nafion/carbon nanotube layer on the tip of a platinized Pt wire. For *N. europaea*, substrate ($NH_4^+$) flux was measured using a microelectrode fabricated by immersing a Ag/AgCl wire in a tapered glass capillary containing electrolyte and a liquid membrane selective for $NH_4^+$.

For all experiments, substrate and/or $O_2$ flux were continuously measured at five positions along the surface of each biofilm for ten minutes unless otherwise indicated (2 mm in the lateral direction between each position; see supplemental FIG. 1). For data concerning physiological flux, all averages represent the arithmetic mean of at least ten minutes of continuous recording at five positions (n=3 replicates), and error bars represent the standard error of the arithmetic mean.

Figure 5A:
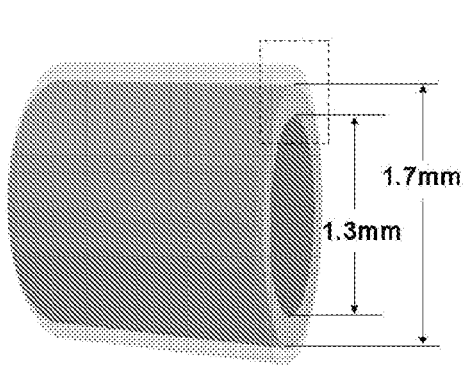
Figure 5B:
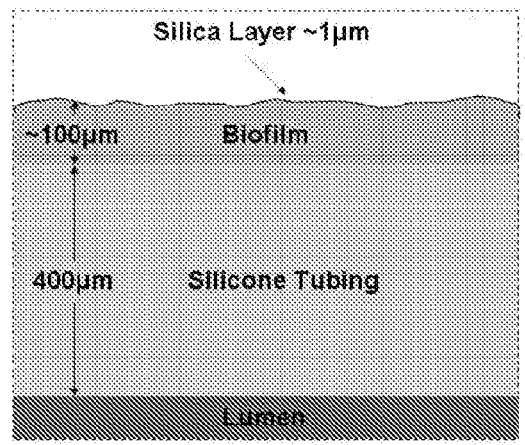

Biofilm Encapsulation: The three acid initiators were screened for biocompatibility with biofilms by continuously measuring real time respiration using oxygen optrodes. Oxygen uptake was monitored for 10 minutes to determine baseline aerobic respiratory level. The media was then carefully removed and filtered media containing 10 µl per ml enriched silica solution was added. The samples were allowed to rest in the saturated silica for 20 minutes in order to encapsulate the biofilm. Oxygen flux measurements were monitored throughout the biosilicification process. After 20 minutes, the solution was again carefully removed and replaced with fresh silica free medium to halt the biosilicification process. Oxygen flux measurements were then continuously recorded along the biofilm surface for 14 hours to monitor biofilm viability. As a control experiment, flux was measured in growth media, the solution was replaced with fresh growth media containing no silica, and physiological flux/viability measured. A diagram illustrating the hollow fiber membrane bioreactor, biofilm, and silica encapsulant is depicted in FIGS. 5A and 5B.

SEM Imaging/Electron Dispersive X-ray (EDX) Elemental Analysis: *P. aeruginosa* and *N. europaea* biofilms were encapsulated with silica as described previously. 30 minutes after biofilm encapsulation, membranes containing encapsulated biofilms were immersed in a 4% glutaraldehyde/sterile phosphate buffer solution for 1 hour. The samples were then soaked in deionized water for 15 minutes, followed by serial dehydration in ethanol solutions (25%, 50%, 75%, 90%, and 100% respectively). Upon removal from the final ethanol wash, the samples were placed in a partially enclosed polystyrene dish and allowed to dry slowly under ambient conditions for 8 hours. Samples were then placed in a desiccating chamber prior to SEM imaging using a FEI NOVA nanoSEM high resolution FESEM.

For EDX analysis, coated biofilms were fixed in 4% glutaraldehyde/sterile phosphate buffer solution for 1 hour, washed four times in deionized water to remove residual media, and dried under ambient conditions for 8 hours. The samples were then placed in a desiccating chamber prior to analysis using an OXFORD INCA 250 electron dispersive X-ray detector (EDX). Spectra were collected over a 120× 120 μm area (n=3). The spectral contribution of carbon was removed prior to analysis due to potential interference from the carbon tape fixative and the atomic percentage of the remaining elements (reported as atomic % (at %)) was determined.

Confocal Imaging: Confocal microscopy was used to quantify membrane integrity after exposure to mineralizing solutions using a BacLight Live/Dead viability kit (Invitrogen Molecular Probes, Carlsbad, Calif.). The stain consisted of a nucleic acid (STYO9) and (propidium iodide) stain, with green and red stained cells representing cells with intact and damaged membranes, respectively. A Zeiss LSM 710 (Thornwood, N.Y.) confocal microscope with multi-wavelength lasers (488 and 514 nm) was used for excitation. Zen software (Zeiss, Thornwood, N.Y.) was used for image capture. Nine cross sections of 144 μm by 144 μm were analyzed over a total biofilm depth of 128 μm (2 μm sections) using a 10× objective lens in immersion oil.

RESULTS

Figure 6A:
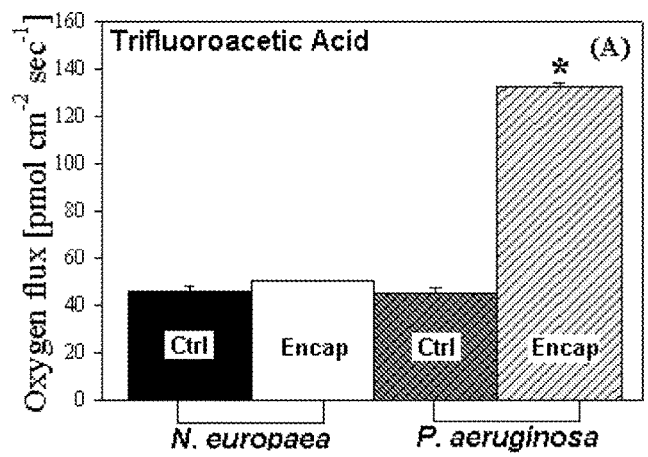
Figure 6B:
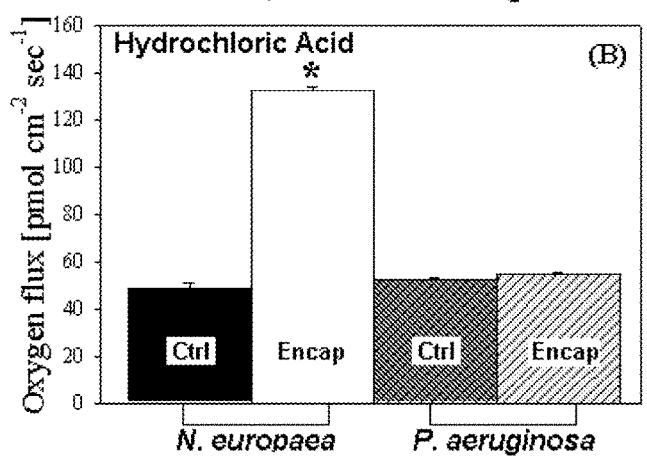
Figure 6C:
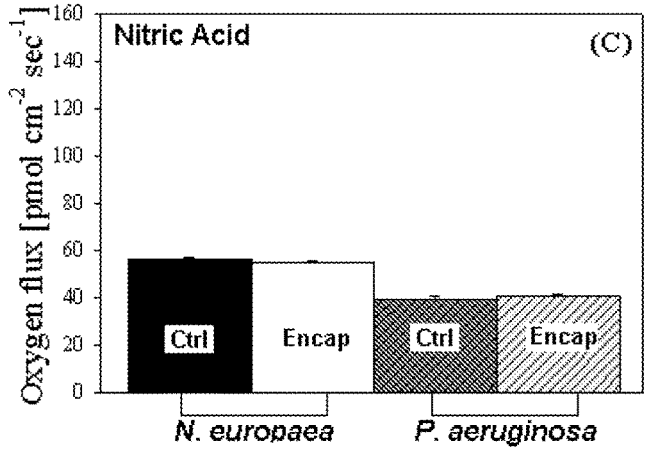

Acid Initiator Screening: Respiratory oxygen flux for *P. aeruginosa* and *N. europaea* biofilms was not significantly different amongst non-encapsulated samples for all experiments (p<0.01, α=0.05) (FIGS. 6A-6C). Additionally, no significant difference in $O_2$ flux was measured during control experiments (fresh growth media with no silica). Trifluoroacetic acid (TFA) significantly increased respiration rate in *P. aeruginosa* biofilms (285±14%), but had no significant effect on *N. europaea* respiration rate (FIG. 6A). This difference could be due to activation of stress response mechanisms expressed by *P. aeruginosa* (e.g., efflux pumps, neutralizing enzymes/antioxidants), which are not present in *N. europaea*. Conversely, hydrochloric acid (HCl) caused a significant increase in average respiratory rate for *N. europaea*, but had no significant effect on *P. aeruginosa* (FIG. 6B). For all samples using nitric acid as the initiator, no significant difference was measured between basal respiratory rate, control samples, and encapsulated biofilms (FIG. 6C). The bacteria respirome is extremely complex, and contains many stress response mechanisms associated with temperature stress, oxidative damage, salt stress, and many other changes in conditions. Although it is unclear as to the specific mechanism(s) behind these increased respiratory rates, no decrease in aerobic respiration was noted during encapsulation with any of the acid initiators. Based on this screening technique, nitric acid was selected as the initiator, although initiation of silicification with TFA and/or HCl should not be ruled out.

Figure 7A:
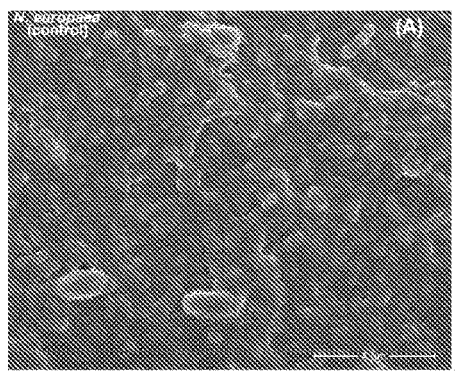
Figure 7B:
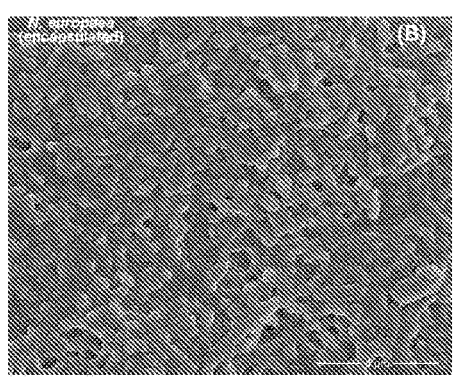
Figure 7C:
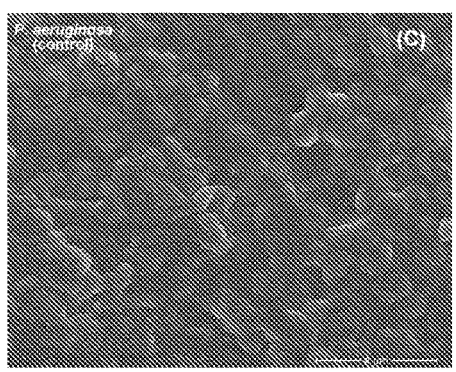
Figure 7D:
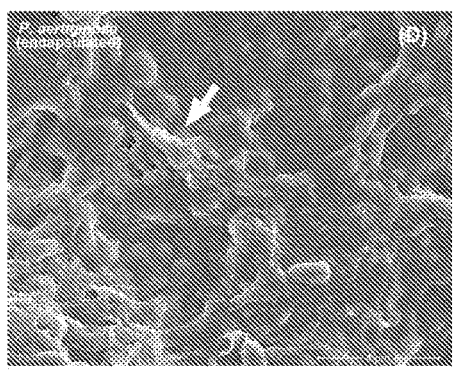

Verification of encapsulation: SEM images of biofilms taken 30 min after encapsulation exhibit morphological differences relative to controls for both *N. europaea* and *P. aeruginosa* (FIGS. 7A-7C). Cells encapsulated in silica retained a higher degree of structural fidelity (FIGS. 7B and 7D, *N. europaea* and *P. aeruginosa*, respectively), resisting the collapsing and smoothing effects of dehydration (FIGS. 7A and 7C, *N. europaea* and *P. aeruginosa*, respectively). In FIG. 7D a silica matrix is bridging adjacent cells (indicated by a white arrow). A thin silica layer coating the exposed surface of the biofilm is apparent. This layer is sufficiently ridged to prevent feature collapse on the microscopic scale while allowing for flexibility of the bulk biofilm. Given that the individual cells are clearly discernable in encapsulated samples, the biomineral layer thickness can be inferred to be on the scale of these cellular surface features (~200 nm--1 μm).

Figures 8A, 8B, 8C, 8D:
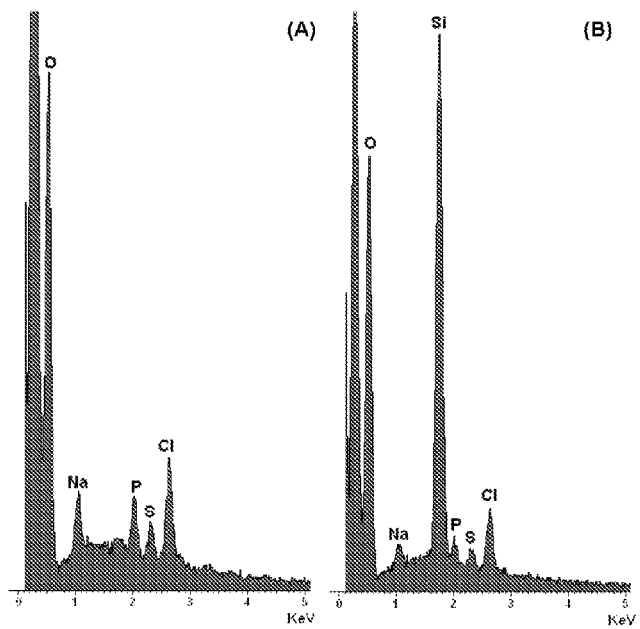

Representative EDX spectra of control and encapsulated biofilms are presented in FIGS. 8A-8C. Samples displayed detectable levels of carbon (C), oxygen (O), silica (Si), phosphorus (P), sulfur (S), sodium (Na), chlorine (Cl) and potassium (K). The elemental contribution from carbon was removed due to potential background artifact and the atomic percentage of the remaining elements was then calculated. Analysis of the biofilm surfaces indicated that silica deposition took place after exposure to mineralizing solutions for 30 minutes, causing an increase in silica concentration from 1.8±0.2% and 0.3±0.6% to 15.2±0.7% and 18.5±0.6% for *P. aeruginosa* and *N. europaea* respectively (Table 1). Surface phosphorous, sulfur, and sodium levels decreased after the encapsulation of both biofilms. These elements are naturally present in both the cellular and extracellular material comprising the biofilm (Beveridge, T. J. et al. (1983) Appl. Environ. Microbiol. 45 (3), 1094-1108; Lunsdorf, H. et al. (1997) J. Bacteriol. 179 (1), 31-40) and tend to be retained even after the extensive washing employed to remove residual media and phosphate buffer (Little, B. et al. (1991) J. Industr. Microbiol. 8 (4), 213-221.

TABLE 1

Average elemental composition (% at) of *P. aeruginosa* and *N. europaea*

| | Si | P | S | Na | Cl | K | O |
|---|---|---|---|---|---|---|---|
| *P. aeruginosa* | | | | | | | |
| Control | 1.8 ± 0.2 | 4.9 ± 0.4 | 2.2 ± 0.3 | 2.5 ± 0.2 | 0 | 0.2 ± 0.4 | 88.3 ± 0.8 |
| Si coated | 15.2 ± 0.7 | 2.0 ± 0.4 | 0.8 ± 0.2 | 1.4 ± 0.5 | 3.5 ± 1.4 | 0.4 ± 0.1 | 76.7 ± 1.0 |
| *N. europaea* | | | | | | | |
| Control | 0.3 ± 0.6 | 2.6 ± 0.4 | 1.7 ± 0.2 | 4.7 ± 0.4 | 5.2 ± 0.7 | 0 | 85.4 ± 1.9 |
| Si coated | 18.5 ± 0.6 | 1.2 ± 0.1 | 1.0 ± 0.1 | 1.3 ± 0.3 | 2.5 ± 0.3 | 0 | 75.5 ± 0.9 |

Figures 9A, 9B:
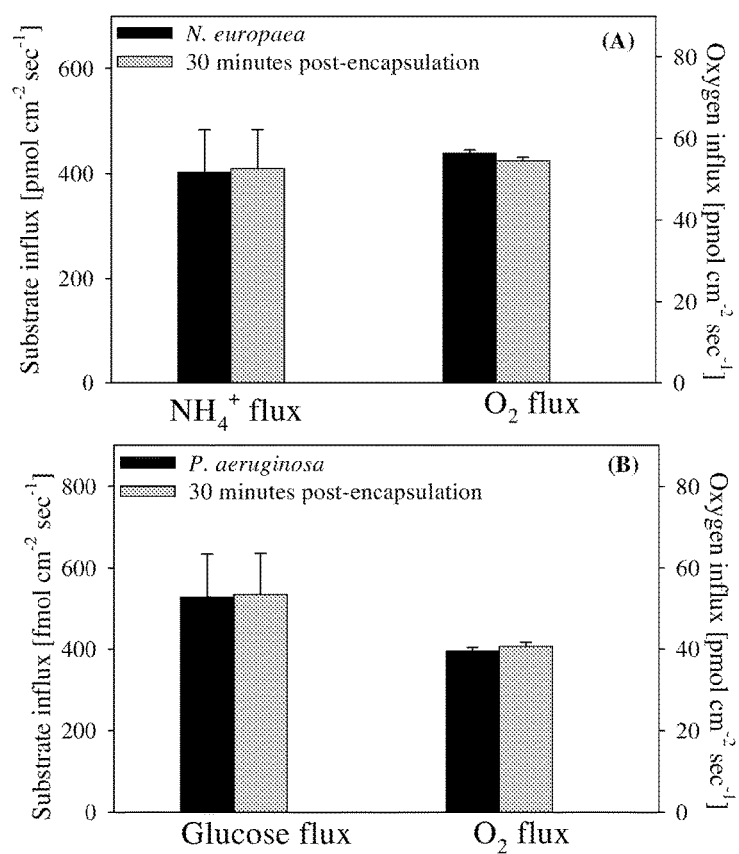

Physiology and viability: Average oxygen and $NH_4^+$ flux for *N. europaea* biofilms did not significantly change following encapsulation using nitric acid as an initiator (FIG. 9A). This result is significant because *N. europaea* has relatively few physiological defense mechanisms and are sensitive to subtle changes in operating conditions (e.g., salt concentration, substrate shock) (Brandt, K.K. et al. (2001) Appl. Environ. Microbiol. 67 (6), 2489-2498; Coci, M. et al. (2005) FEMS Microbiol. Ecol. 53 (3), 359-368). Likewise, metabolic respiratory rates for *P. aeruginosa* did not significantly change after encapsulation using nitric acid (FIG. 9B). No significant differences in metabolic respiration were noted between silicated samples and control samples for either species.

Viability was verified using a membrane integrity stain for all biofilm samples, and no significant difference was noted between control samples and silicated samples.

Discussion: Monocultures of both *P. aeruginosa* and *N. europaea* biofilms were investigated to determine if the encapsulation technology could be applied to organisms exhibiting different species specific stress response mechanisms, substrate and gas requirements, and extracellular matrix composition. *P. aeruginosa* is a model chemoheterotrophic bacterium with a robust set of stress coping mechanisms including efflux pumps, quorum sensing mechanisms, and neutralizing enzymes/antioxidants. In contrast, *N. europaea* is a model chemoautotrophic bacterium that lacks many of these stress response mechanisms and is relatively sensitive to environmental stressors. Biofilms of both species were able to survive silicification and return to normal nutrient and oxygen consumption levels. This finding suggests that the technique may be generalized to a diverse range of biofilm forming bacteria.

The nanostructure of solution-based silica deposits governs the diffusion characteristics of the encapsulant, and can be influenced by several factors including silica concentration, pH, curing temperature, and acid initiator species. In this example, the need to maintain the viability of the living cells constrains parameter type and range that could be varied to influence nanoarchitecture. Temperature and final solution pH had to remain within the organism's optimal growth range, which is especially important for obligate bacteria such as *N. europaea*, which are not capable of utilizing metabolic/proteomic stress response mechanisms to adapt to large changes in environmental conditions. In preliminary experiments, silica concentration was adjusted to provide a window where deposition occurred on the cellular substrate prior to bulk gelation. Given these constraints, three types of acid initiator (hydrochloric, nitric, and trifluoroacetic acid) were screened to determine their effects on biofilm viability.

The respiration rate of cells encapsulated with silica hydrolyzed by nitric acid did not significantly change, while hydrochloric and trifluoracetic acid significantly altered respiration rate within 30 minutes (FIGS. 6A-6C). The increased respiration rate observed in *P. aeruginosa* (using triflouroacetic acid) and *N. europaea* (using hydrochloric acid) may be indicative of oxidative stress. Respiration did not decrease for any of the acid initiators.

The reason for the different response to hydrochloric and trifluoracetic acid is unclear. Acid initiator species can indirectly influence biofilm metabolism by altering the porosity and diffusional characteristics of the silica matrix. Alternatively, the acid may interact directly with the bacteria, stressing the cells. Different bacteria vary in their ability to adapt to acidic environments and the acid type can have specific affects beyond alterations in pH. *P. aeruginosa* are capable of facultative respiration, *N. europaea* are obligate aerobes; thus selection of an acid initiator which can facilitate the encapsulation of a broad range of microbial species is required. To fulfill this requirement, nitric acid initiated silica solutions were chosen for further investigation.

Using nitric acid as an initiator, SEM imaging and EDS elemental analysis confirmed the presence of a silica coating in both species of biofilm (FIGS. 7B and 7D; Table 1). Elemental analysis demonstrated significantly higher concentrations of silica on the surface of encapsulated cells (18.49±0.59 and 15.24±0.67 at % for *N. europaea* and *P. aeruginosa*, respectively) than control samples (Table 1). The small levels of silicon detected in control samples (1.8±0.2 at % and 0.3±0.6 at % (for *P. aeruginosa* and *N. europaea* respectively) may be attributed to the residue left from the silicone tubing utilized to culture the biofilm.

Cellular viability was confirmed using both physiological flux measurements and live/dead staining. Metabolic oxygen, glucose (*P. aeruginosa*), and $NH_4^+$ (*N. europaea*) flux was confirmed after encapsulation with silica (FIG. 4). These results indicated that the silica matrix was sufficiently porous to allow for the diffusion of dissolved gasses and nutrients. Biophysical transport of nutrients and electron acceptors regulates synthesis and maintenance of cells within the biofilm, and is limited by the concentration boundary layer formed at the biofilm-fluid interface. No significant change in oxygen flux, substrate flux, or stoichiometric metabolic ratio was observed after encapsulation ($p<0.02$, $\alpha=0.05$), suggesting that cells survived the encapsulation process intact. No observable differences were noted at 10× or 100× magnification in stained samples analyzed using confocal microscopy. There were no large regions of lysed cells within the matrix (2 μm slices), which one would expect if diffusion limitations or nutrient transport was significantly altered by silica encapsulation. Preservation of physiology and cell viability is particularly important for *N. europaea*, which often limit nitrogen cycling in natural and engineered systems due to the lack of a wide array of stress response mechanisms. Encapsulation of sessile bacteria can potentially improve resistance to shock loading, chemical toxin exposure, and detachment. Such improvements can then be translated into the development of more efficient bioreactors for chemical production and water recovery.

Taken together the results of this study indicate that both persistent *P. aeruginosa* and sensitive *N. europaea* species survive the encapsulation process and retain their viability. Unlike bulk encapsulation processed, the cell-mediated technique generates a thin flexible silica membrane on biofilm surfaces exposed to the surrounding mineralizing solution. Unlike the BioSil methods, silica formation is performed at culture temperatures in solution phase. The thin evenly distributed silica layer does not serve as a barrier to molecular diffusion of $O_2$ or cellular substrate, with no significant variation in physiological flux observed between encapsulated and control biofilms. The silica is also intimately associated with extracellular proteins that reinforce the silica matrix and prevent the cracking observed in bulk encapsulated cellular materials. The formation of the silica layer is dependant upon cellular contact with the mineralizing solution. The technique can therefore be applied to systems with complex geometries so long as solution contact can be maintained during encapsulation. The solution volume can also be expanded for large-scale encapsulation of living cells for industrial and environmental applications.

The cell mediated encapsulation technique is a simple solution based method for encapsulating living cells in a thin porous silica membrane. Monoculture biofilms of the distinct bacterial species *P. aeruginosa* and *N. europaea* were able to maintain physiological flux of $O_2$, glucose (*P. aeruginosa*), and $NH_4^+$ (*N. europaea*) and were determined to be viable by live/dead staining after encapsulation. The cell mediated encapsulation technique employs endogenous extracellular material as a site for deposition. As such it can potentially be applied to a wide range of prokaryotic and eukaryotic cell lines and mixed culture systems. Future work will explore the long term viability of encapsulated biofilms, multi layer biofilm systems, and the application of the technique to other cell lines.

It should be understood, of course, that the foregoing relates to exemplary embodiments of the invention and that modifications may be made without departing from the spirit and scope of the invention as set forth in the following claims.

We claim:

1. A method for encapsulating cells comprising the steps of:
    adding a silica rich sol solution comprising at least one organo-silicon compound, phosphate or serum proteins, and water to cells in a buffered media, wherein a molar silica:water ratio ranges from 4:1 to 40:1, thereby providing a silica-saturated buffered media;
    adjusting said silica-saturated buffered media pH to between 7 and 7.8 for less than 15 minutes;
    monitoring cells for the formation of a silica layer on the cells; and
    isolating the cells from the silica-saturated buffered media after the silica layer is observed at the cell surface but before bulk gelation occurs by removing the cells with the silica layer from said silica-saturated buffered media.

2. The method of claim 1 wherein the cells are individual dissociated cells, cellular clusters, tissue or a combination thereof.

3. The method of claim 1 wherein the cells are mammalian cells.

4. The method of claim 1 wherein the cells are human pancreatic cells.

5. The method of claim 1 wherein the sol solution comprises from about 100 ppm to about 100,000 ppm silica.

6. The method of claim 1 wherein the buffered media comprises from about 80 ppm to about 10,000 ppm of silica after the addition of the silica rich sol solution.

7. The method of claim 1 wherein the cells are monitored for the formation of the silica layer by light microscopy, Raman microscopy, FTIR microscopy, fluorescence microscopy, scanning electric microscopy or energy dispersive x-ray spectroscopy.

8. The method of claim 1 wherein the cells are isolated from the silica-saturated buffered media by diluting the silica-saturated buffered media.

9. The method of claim 1, wherein the silica rich sol solution is alcohol free.

10. The method of claim 1, wherein a porous silica layer is formed on the cells.

11. The method of claim 10, wherein the porous silica layer is 100 nm to several microns in thickness.

12. The method of claim 1, wherein the molar silica:water ratio is selected to completely hydrolyze the organo-silicon compound and slow the poly-condensation of silica into a solid mass.

13. The method of claim 1, wherein said silica-saturated buffered media has the pH value that is tolerant by the cells to be encapsulated.

* * * * *